United States Patent
Richardson et al.

(10) Patent No.: US 6,764,484 B2
(45) Date of Patent: Jul. 20, 2004

(54) C-CHANNEL TO O-CHANNEL CONVERTER FOR A SINGLE OPERATOR EXCHANGE BILIARY CATHETER

(75) Inventors: Kevin Richardson, Hopkinton, MA (US); Michael Mangano, Medfield, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 99 days.

(21) Appl. No.: 09/822,708

(22) Filed: Mar. 30, 2001

(65) Prior Publication Data

US 2002/0143251 A1 Oct. 3, 2002

(51) Int. Cl.[7] .............................................. A61M 25/00
(52) U.S. Cl. .................................................... 604/523
(58) Field of Search ...................... 604/93, 158, 164.01, 604/164.13, 167.01–167.05; 600/433–435, 585

(56) References Cited

U.S. PATENT DOCUMENTS

| | | | |
|---|---|---|---|
| 1,204,053 A | 11/1916 | Moore | |
| 2,623,520 A | 12/1952 | Bamford, Jr. et al. | 128/221 |
| 3,015,869 A | 1/1962 | Rapata | 24/213 |
| 3,536,281 A | 10/1970 | Meehan et al. | 248/73 |
| 4,345,606 A | 8/1982 | Littleford | 128/784 |
| RE31,855 E | 3/1985 | Osborne | 604/161 |
| 4,696,668 A | 9/1987 | Wilcox | 604/28 |
| 4,748,982 A | 6/1988 | Horzewski et al. | 128/344 |
| 4,762,129 A | 8/1988 | Bonzel | 606/194 |
| 4,771,777 A | 9/1988 | Horzewski et al. | 128/344 |
| 4,781,677 A | 11/1988 | Wilcox | 604/28 |

(List continued on next page.)

FOREIGN PATENT DOCUMENTS

| | | |
|---|---|---|
| DE | 41 15 007 A1 | 11/1992 |
| EP | 0 328 760 A2 | 8/1989 |
| EP | 0 388 112 A2 | 9/1990 |
| EP | 0 792 657 A2 | 9/1997 |
| EP | 0 801 955 B1 | 10/1997 |
| WO | WO 92/03963 | 3/1992 |
| WO | WO 96/33764 | 10/1996 |
| WO | WO 98/10820 | 3/1998 |
| WO | WO 98/10821 | 3/1998 |
| WO | WO 99/59664 | 11/1999 |
| WO | WO 00/69499 | 11/2000 |
| WO | WO 00/69500 | 11/2000 |
| WO | WO 01/66178 A1 | 9/2001 |

OTHER PUBLICATIONS

Knecht, Gregory L., M.D. et al., "Double–Channel Fistulotome For Endoscopic Drainage of Pancreatic Pseudocyst", *Gastrointestinal Endoscopy*, vol. 37, No. 3, May/Jun. 1991, pp. 356–357.

Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438–440.

*Primary Examiner*—Manuel Mendez
(74) *Attorney, Agent, or Firm*—Crompton, Seager & Tufte, LLC

(57) ABSTRACT

A catheter system for use during biliary procedures, including a first elongate member carrying a guidewire lumen, and a channel extending longitudinally along the member which provides access to the guidewire lumen and defines two edge surfaces. A second elongate member is also included which is disposed within the guidewire lumen and mates with the cross-sectional profile of the guidewire lumen of the first elongate member, thereby converting a guidewire lumen having a C-shaped design into one having an O-shaped design. The catheter may be used in rapid exchange catheter procedures requiring the use of small diameter guidewires which would otherwise slip out of the channel during use.

17 Claims, 15 Drawing Sheets

U.S. PATENT DOCUMENTS

| | | | |
|---|---|---|---|
| 4,835,824 A | 6/1989 | Durham et al. | 24/339 |
| 4,844,092 A | 7/1989 | Rydell et al. | 128/772 |
| 4,900,184 A | 2/1990 | Cleveland | 403/397 |
| 4,905,667 A | 3/1990 | Foerster et al. | 128/4 |
| 4,917,103 A | 4/1990 | Gambale et al. | 128/772 |
| 4,927,418 A | 5/1990 | Dake et al. | 604/264 |
| 4,928,693 A | 5/1990 | Goodin et al. | 128/637 |
| 4,932,413 A | 6/1990 | Shockey et al. | 128/657 |
| 4,946,443 A | 8/1990 | Hauser et al. | 604/165 |
| 4,983,168 A | 1/1991 | Moorehead | 604/161 |
| 4,988,356 A | 1/1991 | Crittenden et al. | 606/192 |
| 4,997,421 A | 3/1991 | Palsrok et al. | 604/174 |
| 5,040,548 A | 8/1991 | Yock | 128/898 |
| 5,061,273 A | 10/1991 | Yock | 606/194 |
| 5,064,414 A | 11/1991 | Revane | 604/165 |
| 5,125,915 A | 6/1992 | Berry et al. | 604/23 |
| 5,135,535 A | 8/1992 | Kramer | 606/194 |
| 5,147,377 A | 9/1992 | Sahota | 606/194 |
| 5,158,545 A | 10/1992 | Trudell et al. | 604/53 |
| 5,167,634 A | 12/1992 | Corrigan, Jr. et al. | 604/160 |
| 5,195,978 A | 3/1993 | Schiffer | 604/161 |
| 5,205,822 A | 4/1993 | Johnson et al. | 604/96 |
| 5,232,445 A | 8/1993 | Bonzel | 604/96 |
| 5,248,306 A | 9/1993 | Clark et al. | 604/283 |
| 5,250,033 A | 10/1993 | Evans et al. | 604/160 |
| 5,255,690 A | 10/1993 | Keith et al. | 128/772 |
| 5,279,562 A | 1/1994 | Sirhan et al. | 604/96 |
| 5,282,479 A | 2/1994 | Havran | 128/772 |
| 5,290,232 A | 3/1994 | Johnson et al. | 604/96 |
| 5,290,241 A | 3/1994 | Kraus et al. | 604/161 |
| 5,300,085 A | 4/1994 | Yock | 606/191 |
| 5,306,247 A | 4/1994 | Pfenninger | 604/96 |
| 5,308,318 A | 5/1994 | Plassche, Jr. | 604/54 |
| 5,320,602 A | 6/1994 | Karpiel | 604/54 |
| 5,324,259 A | 6/1994 | Taylor et al. | 604/96 |
| 5,324,269 A | 6/1994 | Miraki | 604/160 |
| 5,328,472 A | 7/1994 | Steinke et al. | 604/102 |
| 5,334,143 A | 8/1994 | Carroll | 604/54 |
| 5,334,187 A | 8/1994 | Fischell et al. | 604/194 |
| 5,350,395 A | 9/1994 | Yock | 606/194 |
| 5,364,355 A | 11/1994 | Alden et al. | 604/96 |
| 5,364,376 A | 11/1994 | Horzewski et al. | 604/280 |
| 5,370,623 A | 12/1994 | Kreamer | 604/165 |
| 5,389,087 A | 2/1995 | Miraki | 604/247 |
| 5,397,302 A | 3/1995 | Weaver et al. | 604/54 |
| 5,451,233 A | 9/1995 | Yock | 606/194 |
| 5,454,790 A | 10/1995 | Dubrul | 604/104 |
| 5,458,584 A | 10/1995 | Ginn et al. | 604/280 |
| 5,458,605 A | 10/1995 | Klemm | 606/108 |
| 5,462,530 A | 10/1995 | Jang | 604/160 |
| 5,480,389 A | 1/1996 | McWha et al. | 604/165 |
| 5,489,271 A | 2/1996 | Andersen | 604/102 |
| 5,490,837 A | 2/1996 | Blaeser et al. | 604/96 |
| 5,496,346 A | 3/1996 | Horzewski et al. | 606/154 |
| 5,501,227 A | 3/1996 | Yock | 128/662.06 |
| 5,516,336 A * | 5/1996 | McInnes et al. | 606/194 |
| 5,531,700 A | 7/1996 | Moore et al. | 604/164 |
| 5,536,248 A | 7/1996 | Weaver et al. | 604/54 |
| 5,540,236 A | 7/1996 | Ginn | 128/772 |
| 5,599,299 A | 2/1997 | Weaver et al. | 604/54 |
| 5,599,300 A | 2/1997 | Weaver et al. | 604/54 |
| 5,613,949 A | 3/1997 | Miraki | 604/101 |
| 5,626,600 A | 5/1997 | Horzewski et al. | 606/194 |
| 5,706,827 A | 1/1998 | Ehr et al. | 128/772 |
| 5,725,504 A | 3/1998 | Collins | 604/165 |
| 5,788,681 A | 8/1998 | Weaver et al. | 604/280 |
| 5,800,414 A | 9/1998 | Cazal | 604/280 |
| 5,833,706 A | 11/1998 | St. Germain et al. | 606/194 |
| 5,843,028 A | 12/1998 | Weaver et al. | 604/54 |
| 5,849,016 A | 12/1998 | Suhr | 606/108 |
| 5,921,971 A | 7/1999 | Agro et al. | 604/280 |
| 6,007,522 A | 12/1999 | Agro et al. | 604/264 |
| 6,059,748 A | 5/2000 | Teirstein et al. | 604/53 |
| 6,096,009 A | 8/2000 | Windheuser et al. | 604/165 |
| 6,106,487 A | 8/2000 | Duane et al. | 600/585 |
| 6,152,910 A | 11/2000 | Agro et al. | 604/523 |
| 6,346,093 B1 * | 2/2002 | Allman et al. | 604/167.06 |
| 6,520,951 B1 * | 2/2003 | Carrillo, Jr. et al. | 604/516 |

* cited by examiner

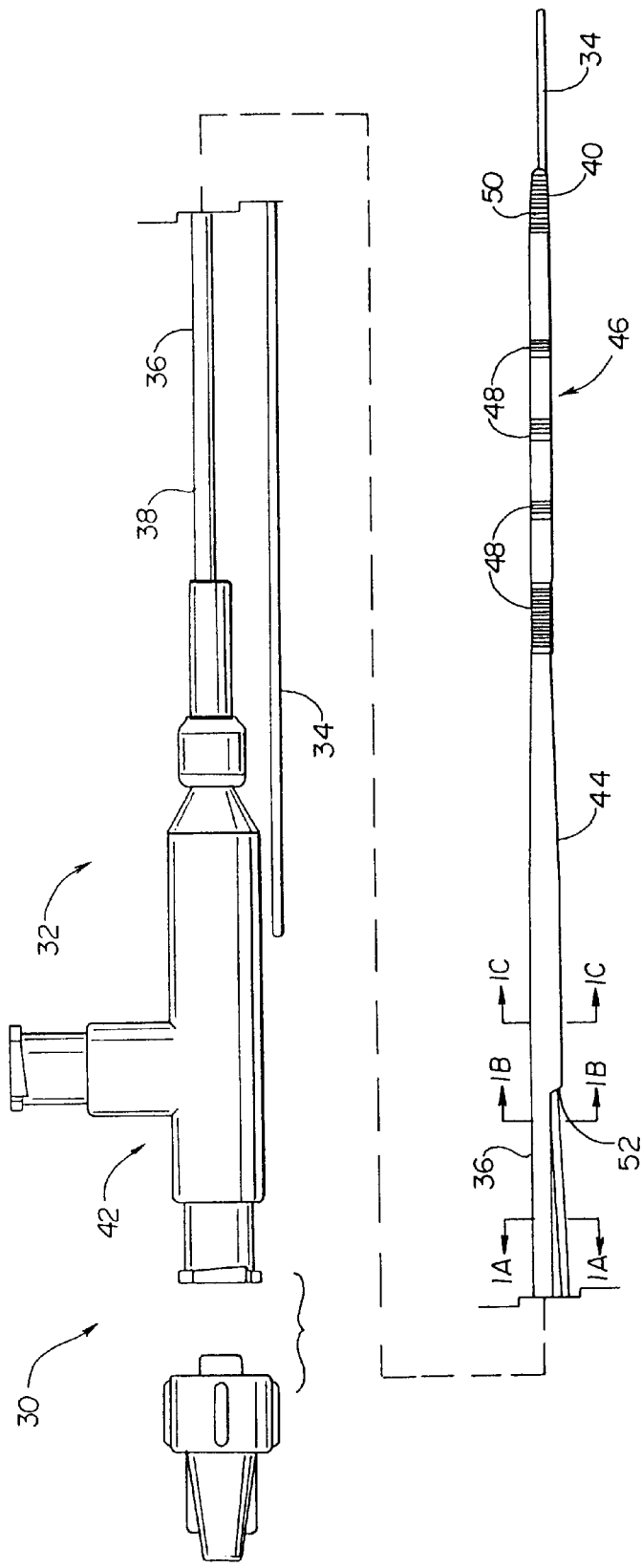

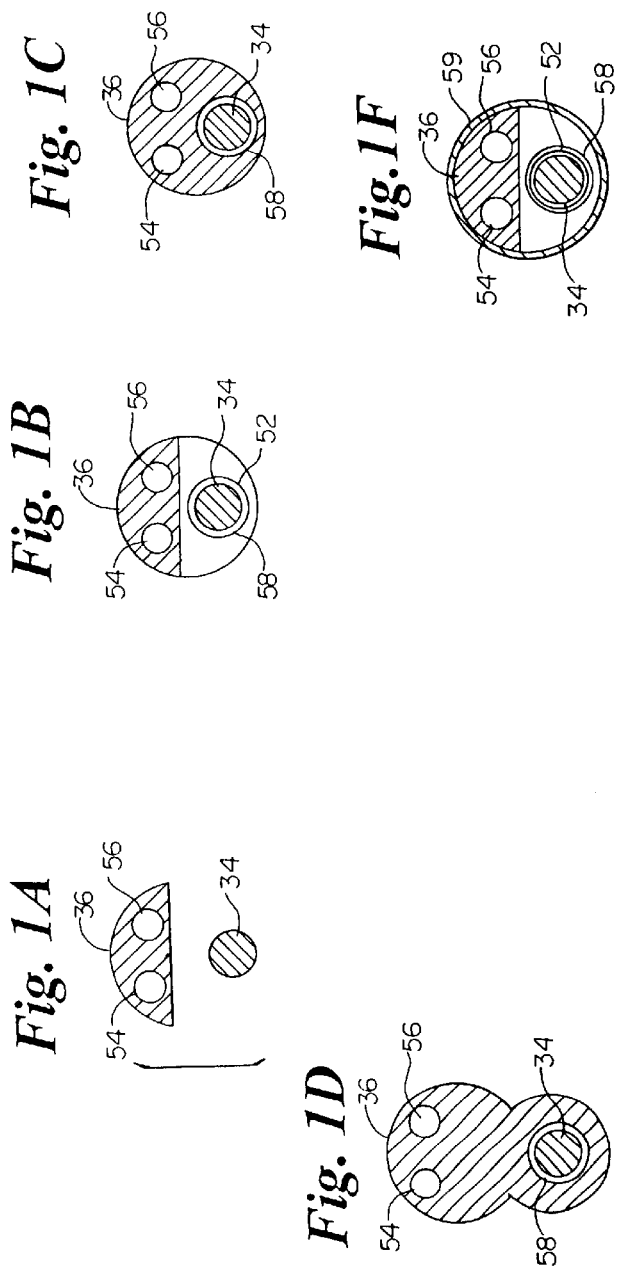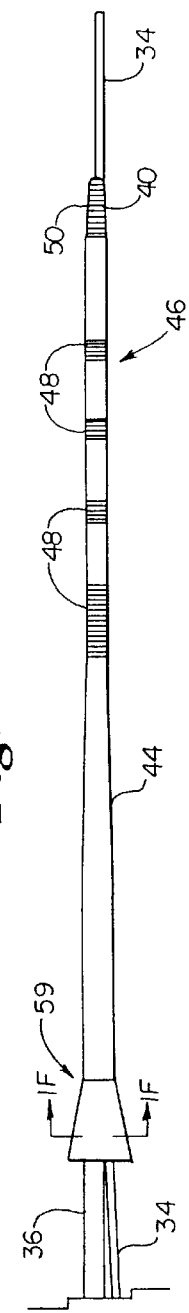

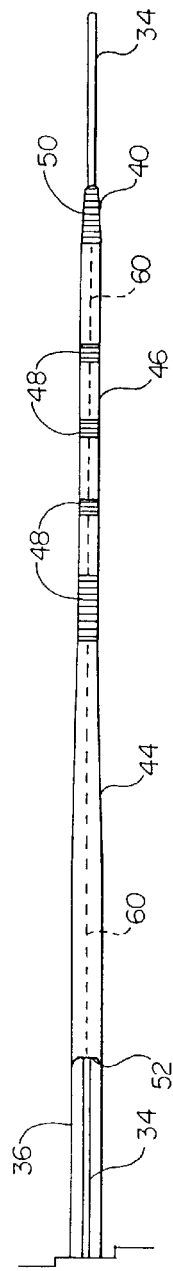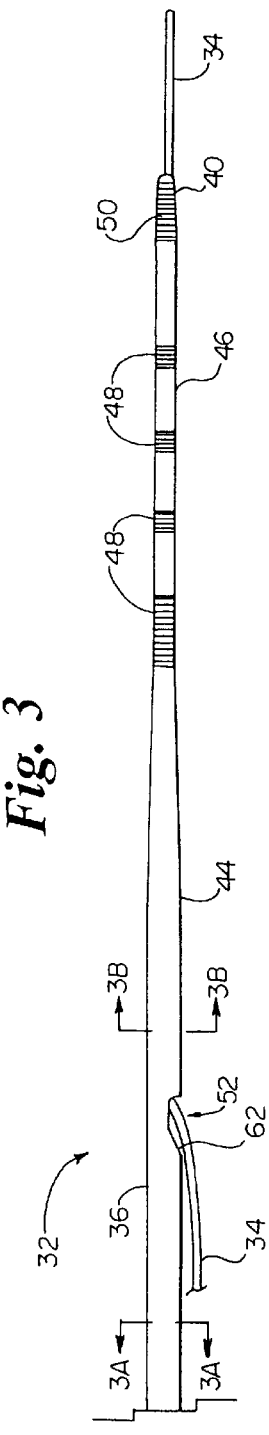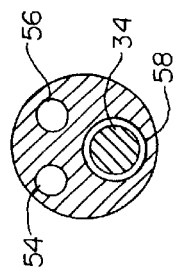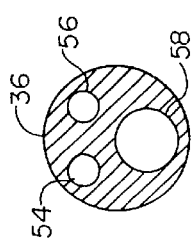
Fig. 2
Fig. 3
Fig. 3A
Fig. 3B

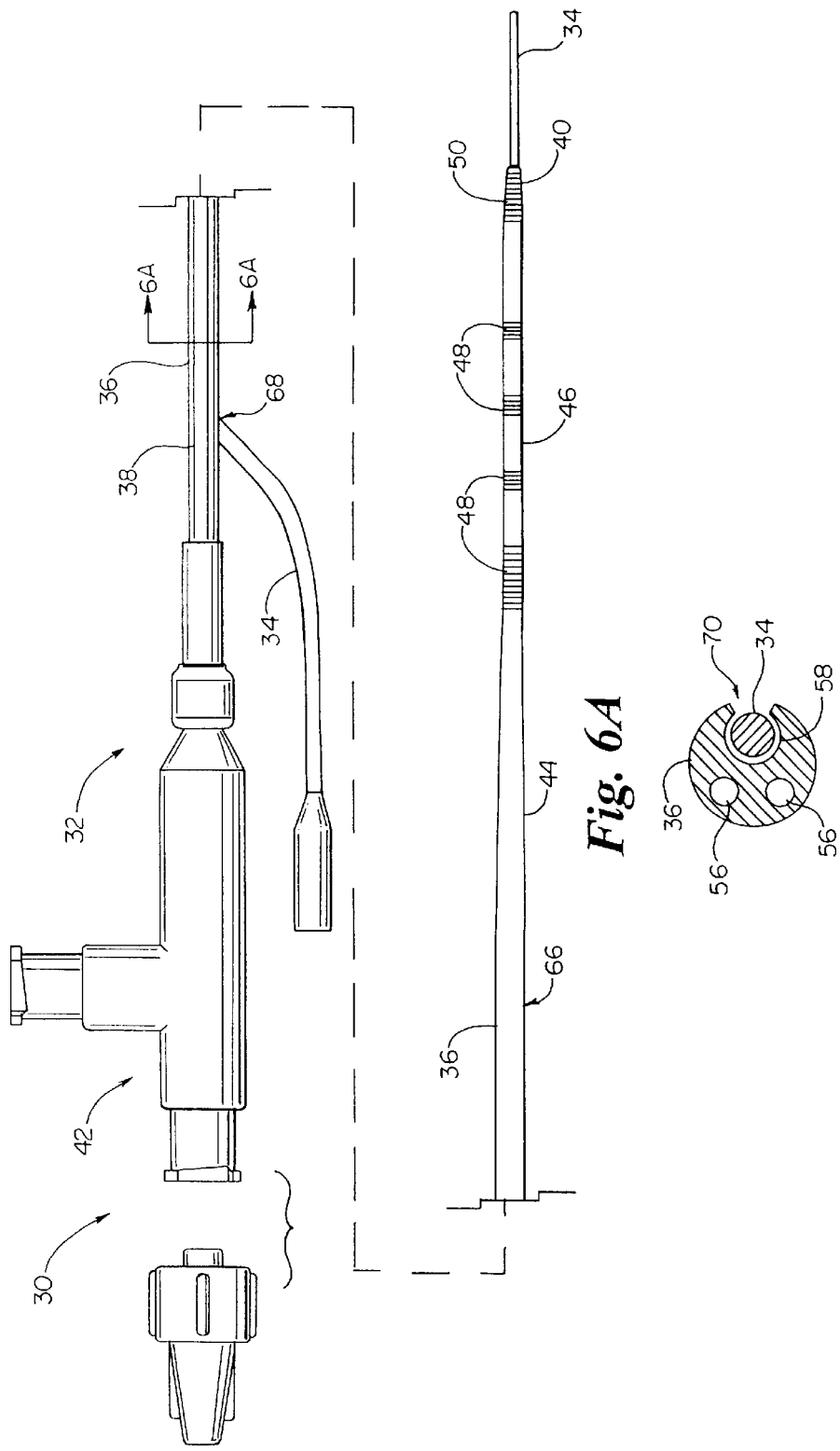

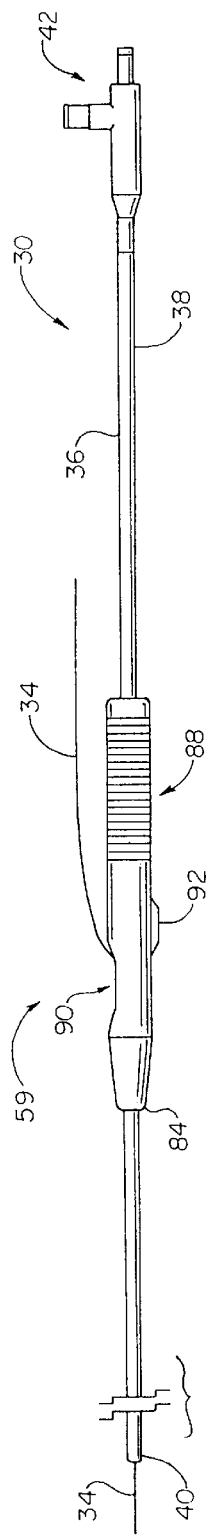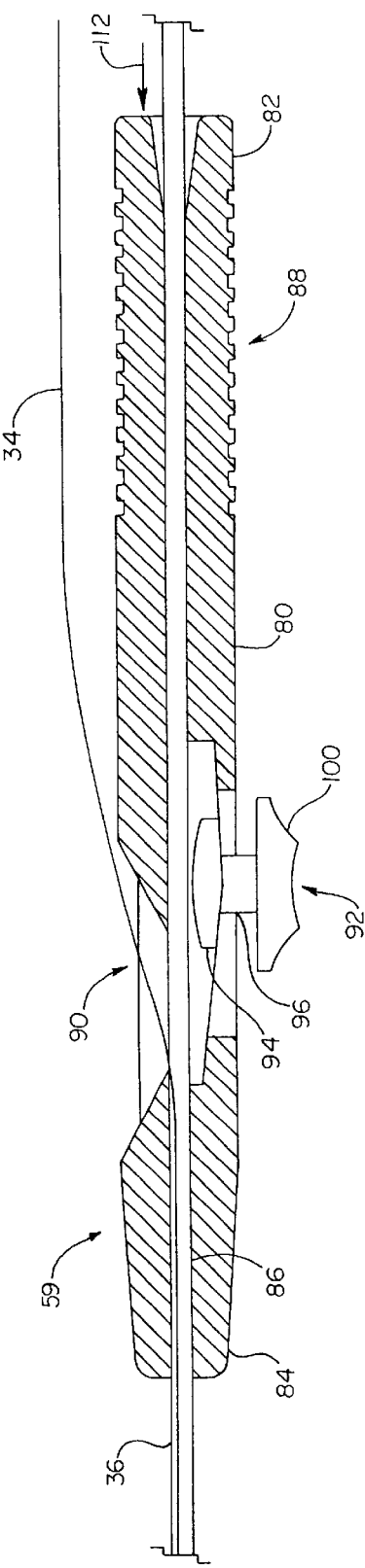
Fig. 7G
Fig. 7H

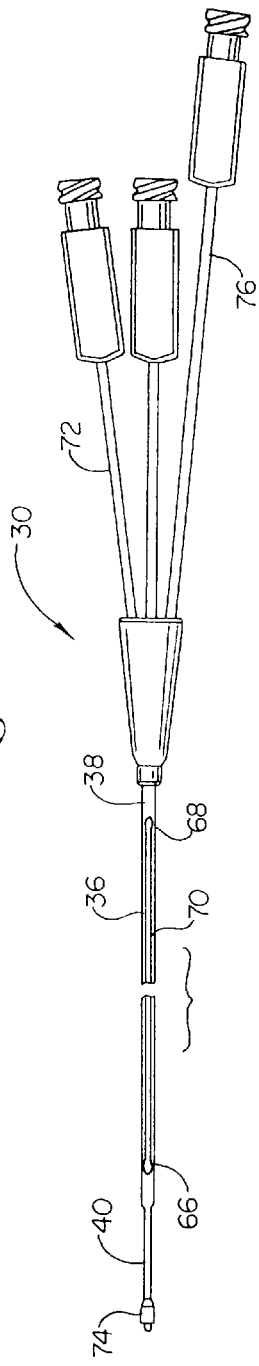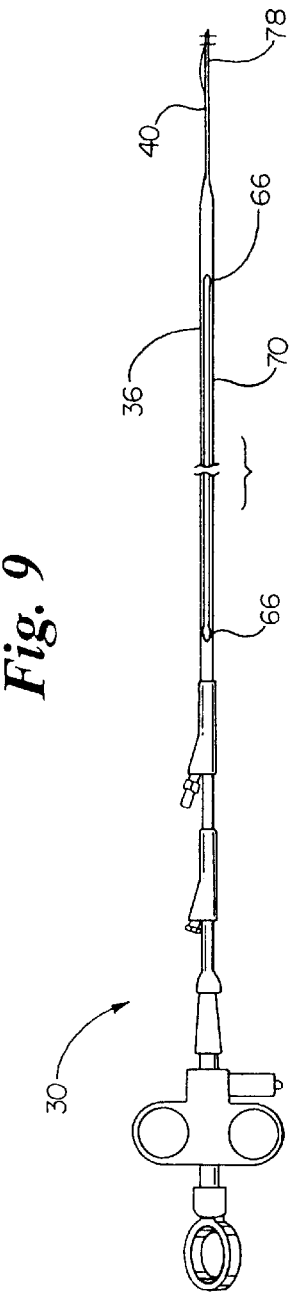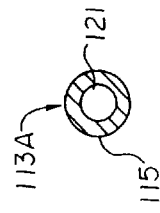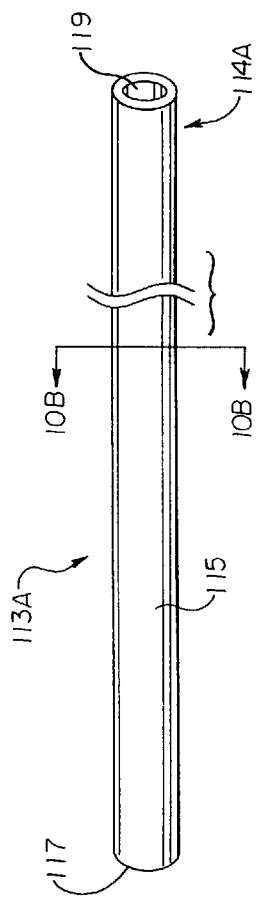

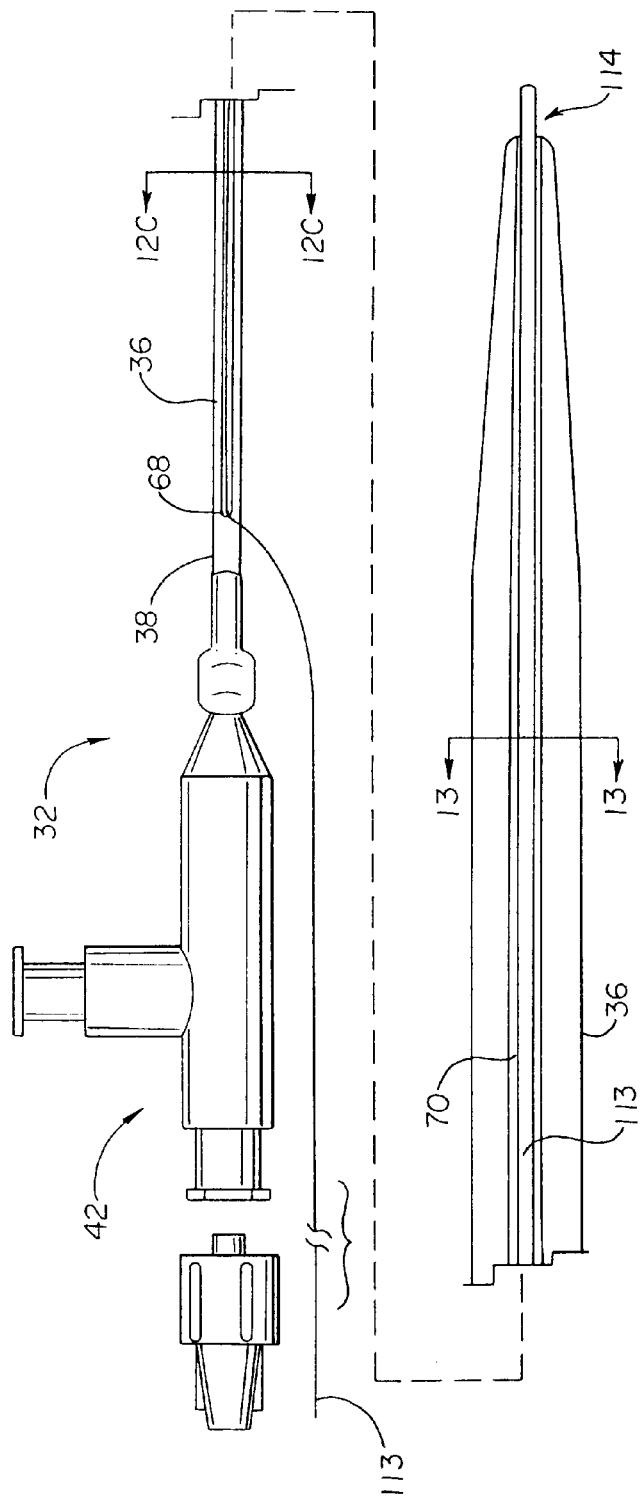

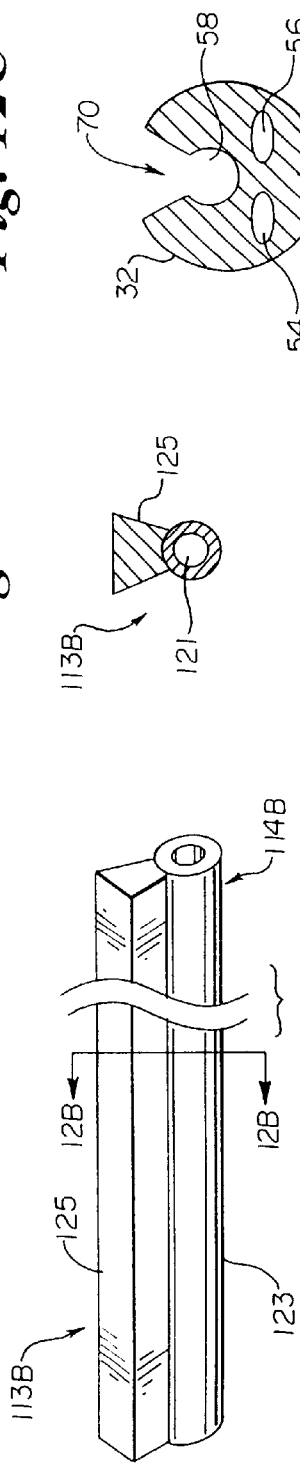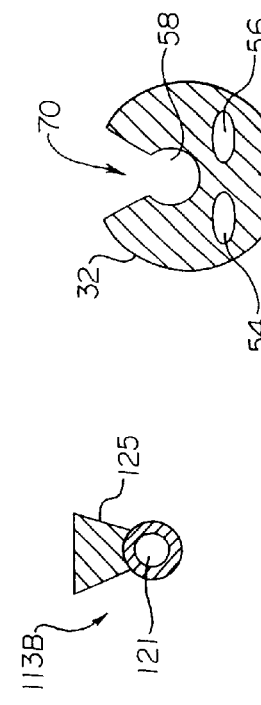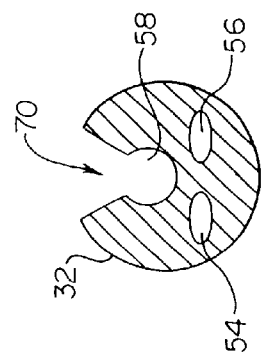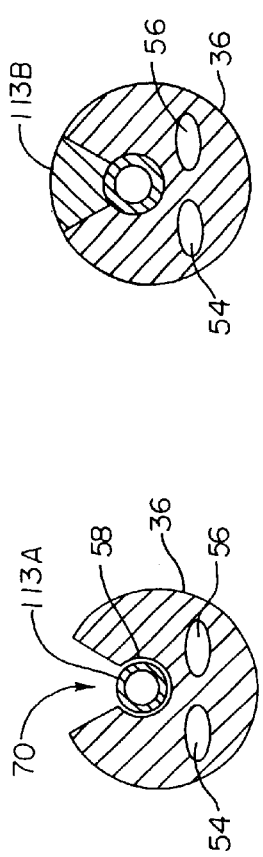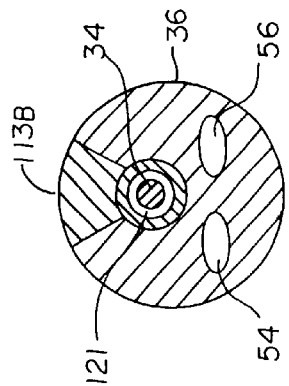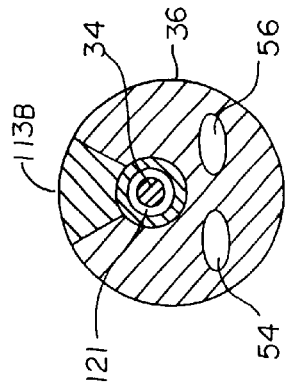

C-CHANNEL TO O-CHANNEL CONVERTER FOR A SINGLE OPERATOR EXCHANGE BILIARY CATHETER

FIELD OF THE INVENTION

The present invention generally relates to biliary catheters and methods of use. More specifically, the present invention relates to single operator exchange biliary catheters and associated ancillary devices.

DESCRIPTION OF THE PRIOR ART

Endoscopic procedures for treating abnormal pathologies within the alimentary canal system and biliary tree (including the biliary, hepatic, and pancreatic ducts) are increasing in number. The endoscope provides access to the general area of a desired duct using direct visualization, however, the duct itself must be navigated using a catheter in conjunction with fluoroscopy and guidewires.

Catheters are known for treatment of targeted anatomical regions. Known methods and devices for using biliary catheters for accessing the biliary tree for performing catheter procedures are disclosed in Weaver et al., U.S. Pat. No. 5,397,302 and Karpiel, U.S. Pat. No. 5,320,602, the disclosures of which are herein incorporated by reference.

In general, for treatment of an abnormal pathology within a patient's biliary tree, an endoscope is first introduced into the mouth of the patient. The endoscope includes a proximal end and a distal end, and has a lumen extending longitudinally between the proximal and the distal ends. The endoscope is guided through the patient's alimentary tract or canal until an opening at the distal end of the endoscope is proximate the location for gaining access to the area to receive treatment. At this point, the endoscope allows for other components, such as a catheter, to access the targeted area.

For visualization or treatment within the biliary tree, the distal end of the endoscope is positioned proximate the papilla of vater leading to the common bile duct and the pancreatic duct. A catheter is guided through the lumen of the endoscope until a distal tip of the catheter emerges from the opening at the distal end of the endoscope.

The catheter maybe used for accessing the biliary tree. The distal end of the catheter is guided through the orifice to the papilla of vater (located between the sphincter of oddi) leading to the common bile duct and the pancreatic duct. A guidewire may be used for further accessing a desired location within the biliary tree. The guidewire is inserted in an opening at a proximal end of the catheter and guided through the catheter until it emerges from the distal end of the catheter.

If visualization of the common bile duct is desired, the guidewire is guided into the common bile duct. The catheter is advanced over the guidewire, as previously described, until the distal end of the catheter is positioned in the common bile duct at the desired location. The catheter is now in position for delivery of contrast media for fluoroscopic visualization of anatomical detail within the common bile duct. Once the guidewire is placed, it is desirable to maintain position of the guidewire during subsequent catheter procedures, including catheter exchange procedures.

Present biliary endoscopic procedures include the use of multi-lumen catheters for endoscopic retrograde cholangiopancreatography, endoscopic retrograde sphincterotomy, the use of balloon catheters having retrieval balloons, and other therapeutic and diagnostic procedures. As described in general above, these present biliary endoscopic procedures are performed using guidewire techniques. The present devices utilized in these procedures are at least 180 cm long since they pass through the endoscope, which is commonly at least 150 cm long. Therefore, when using a standard catheter having a guidewire lumen extending the full length of the catheter, guidewires used during these procedures must be at least 400 cm in length to accommodate the exchanging of different devices while maintaining access and position within the biliary tree. The exchange of devices over a 400 cm guidewire is both time consuming and cumbersome.

Due to the length of the guidewire, physicians require at least two assistants in the room to perform the biliary endoscopic procedure. Typically, one assistant is responsible for the patient and device-related concerns, while the other assistant is responsible for the guidewire. The additional hands required due to the length of the guidewire results in a relatively more time consuming and costly procedure.

The present invention provides rapid exchange biliary catheters which may include a guidewire lumen having a C-shaped channel through which the guidewire is disposed. This design may not allow for the use of very small guidewires, such as a 0.018-inch diameter guidewire, if the wire diameter is smaller than the channel. Thus, the physician may face a limited choice of guidewire sizes for use in a biliary procedure when some types of rapid exchange catheters are being utilized.

It is desirable to have an exchange catheter suitable for use within the alimentary canal for accessing targeted anatomical regions, such as the biliary tree, having features which facilitate rapid exchange and allow an exchange procedure to be performed by a single operator. It is desirable to have a biliary exchange catheter which may be used in connection with a shorter guidewire, and requires less personnel for performing biliary procedures. It is desirable to have a biliary exchange catheter which limits the amount of guidewire over which the catheter must travel.

It is also desirable to have a biliary rapid exchange catheter which may be convertible for use between conventional guidewire techniques and rapid exchange guidewire techniques. It is desirable to have a biliary rapid exchange catheter which is easily removable from the guidewire, and adaptable for use with most catheter systems used within the alimentary canal.

It would also be desirable to have a rapid exchange catheter which would allow for the use of small diameter guidewires, such as a 0.018-inch guidewire, without the risk of the guidewire slipping out of the guidewire lumen through the channel.

SUMMARY OF THE INVENTION

The present invention relates to a biliary catheter for use in biliary endoscopic procedures which incorporates rapid exchange catheter features. Rapid exchange features include an effective guidewire lumen which is much shorter than the overall catheter length to facilitate rapid exchange of the device over the guidewire.

In one preferred embodiment, the present invention is an improved catheter for use in biliary procedures which includes a shaft having a proximal end and a distal end. The improvement includes a guidewire lumen carried by the shaft extending from a location proximal of the distal end of the shaft to a location proximate the distal end of the shaft. Means are provided for accessing the guidewire lumen from a location exterior to the catheter shaft, located a substantial distance distal of the proximal end of the shaft.

The guidewire lumen may be formed integral with the shaft. The means for accessing the guidewire lumen may include an opening extending through the wall of the catheter shaft. Additionally, the wall of the catheter shaft defined by the guidewire lumen may include a relatively weak area extending longitudinally between the opening and the distal end of the shaft. The weak area may be perforated. The catheter may further include a tool for guiding a guidewire through the opening into the guidewire lumen.

In a further preferred embodiment, the means for accessing the lumen may include a slit in the wall of the catheter shaft. An ancillary lumen may extend between the catheter proximal end and the catheter distal end.

In one embodiment, the means for accessing the guidewire lumen includes a first opening or intermediate guidewire port through the wall of the catheter shaft into the guidewire lumen located proximal of the distal end of the shaft. A second opening or proximal guidewire port into the guidewire lumen is located proximal of the first opening. A channel extends between the first opening and the second opening. The channel includes a longitudinal opening to the exterior of the catheter shaft extending between the first opening and the second opening in communication with the guidewire lumen. The longitudinal opening preferably is smaller than the diameter of a guidewire used therewith.

In another embodiment, the present invention is a biliary rapid exchange catheter. The biliary rapid exchange catheter includes a biliary catheter sized for passage within an endoscope including a shaft having a proximal end and a distal end. The biliary catheter includes a tubular member having a proximal end, a distal end, and a guidewire lumen extending longitudinally therethrough which extends between a location proximate the distal end of the shaft (a distal port) to a location proximal of the distal end of the shaft (a proximal port). The proximal port is provided in communication with the guidewire lumen, at a location proximal of the distal end of the shaft.

The proximal port may be located at the proximal end of the tubular member. The guidewire lumen may then extend between the proximal end and the distal end of the shaft. The guidewire lumen would then include a weakened area extending longitudinally between the proximal port and the distal end of the shaft. The biliary catheter may further include an ancillary lumen extending between the proximal end and the distal end of the shaft.

The biliary catheter may alternatively include an intermediate port into the guidewire lumen at a longitudinal location between the proximal port and the distal end of the shaft or distal port. Means are included extending longitudinally between the proximal port and the intermediate port for allowing a guidewire to be moved between a location exterior of the guidewire lumen to a location within the guidewire lumen between the proximal and intermediate ports. The means for allowing the guidewire to be moved between a location exterior the guidewire lumen and within the guidewire lumen include an open channel extending longitudinally between the proximal port and the intermediate port.

The means for allowing the guidewire to be moved between a location exterior the guidewire lumen and within the guidewire lumen may include a weakened portion within the tubular member extending longitudinally between the proximal port and the intermediate port. The weakened portion may be perforated.

The biliary rapid exchange catheter may also include a second tubular member having a cross-sectional profile which serves to convert the channel of the catheter from a C-shaped design to an O-shaped design. The tubular member is inserted through the channel and into the guidewire lumen, and is extended longitudinally therein. The tubular member includes a lumen for receiving a guidewire.

In another embodiment, the present invention includes a method of positioning a biliary catheter including a shaft having a proximal end and a distal end, within a patient's alimentary canal. The method includes the step of providing a catheter with a guidewire lumen therein. The guidewire lumen extends from a location proximal of the distal end of the shaft to a location proximate the distal end of the shaft. A port is provided through a sidewall of the shaft into the guidewire lumen. The port is located distal of the proximal end of the shaft. The method further includes the step of moving a guidewire through the port, relative to the shaft. The method may further include the step of advancing the catheter over the guidewire.

In another embodiment, the present invention includes a method of exchanging a catheter during a biliary endoscopic procedure. The method includes the step of passing an endoscope having a lumen extending longitudinally therethrough, through a patient's mouth into the alimentary canal. A distal end of the endoscope is positioned proximate an opening into the biliary tree. A guidewire is passed through the lumen of the endoscope.

A catheter is provided having a guidewire lumen carried by the shaft, extending from a location proximal of a distal end of the shaft to a location proximate the distal end of the shaft. A first opening is included into the guidewire lumen, located distal of the proximal end of the shaft. The catheter is advanced over the guidewire, wherein a proximal end of the guidewire exits the first opening.

The method may further include retracting the catheter over the guidewire. In one embodiment, wherein the catheter is retracted over the guidewire until the opening is outside the proximal end of the endoscope, the catheter has a weakened area extending longitudinally between the opening and the distal end of the catheter. The method further comprises the step of peeling the catheter away from the guidewire.

The catheter may further include a second opening or intermediate opening into the guidewire lumen. A channel extends longitudinally between the first opening and the second opening. The method further comprises the step of passing the guidewire radially through the channel opening while inserting or retracting the catheter until the guidewire exits the second opening.

In one embodiment, the present invention additionally includes a method of exchanging guidewires during a biliary endoscopic procedure. The method includes the step of inserting a second tubular member having a lumen through the channel into the guidewire lumen and advancing it longitudinally therein before advancing the catheter over the guidewire

BRIEF DESCRIPTION OF THE DRAWINGS

The invention will be further described with reference to the accompanying drawings, wherein like numbers refer to like parts in several views and wherein:

FIG. 1 is a partial elevational view of a catheter in accordance with the present invention having a guidewire lumen for facilitating rapid catheter exchange with a guidewire passing therethrough;

FIG. 1A is a cross-sectional view of the catheter of FIG. 1 taken along line 1A—1A;

FIG. 1B is a cross-sectional view of the catheter of FIG. 1 taken along line 1B—1B;

FIG. 1C is a cross-sectional view of the catheter of FIG. 1 taken along line 1C—1C;

FIG. 1D is a cross-sectional view of an alternative embodiment of the catheter of FIG. 1 in accordance with the present invention, also taken along line 1C—1C;

FIG. 1E is a partial elevational view of an alternative embodiment of the catheter in accordance with the present invention;

FIG. 1F is a cross-sectional view of the catheter of FIG. 1E taken along line 1F—1F;

FIG. 2 is a partial elevational view of another embodiment of the catheter in accordance with the present invention;

FIG. 3 is a partial elevational view of another embodiment of the catheter in accordance with the present invention;

FIG. 3A is a cross-sectional view of the catheter of FIG. 3 taken along line 3A—3A;

FIG. 3B is a cross-sectional view of the catheter of FIG. 3 taken along line 3B—3B;

FIG. 6 is a different partial elevational view of the catheter of FIG. 5 having a guidewire disposed therein;

FIG. 6A is a cross-sectional view of the catheter of FIG. 6 taken along line 6A—6A showing the guidewire received within the lumen of FIG. 5;

FIG. 7G is a partial elevational view of a catheter assembly showing an application of the present invention;

FIG. 7H is a partial cross-sectional view of the catheter of FIG. 7 taken along line 7B—7B, showing a fourth guidewire tool position; and FIG. 8 is a partial elevational view of a catheter showing another application of the present invention;

FIG. 9 is a partial elevational view of a catheter showing another application of the present invention;

FIG. 10A is a partial elevational view of a tubular member which may be disposed within the catheter's guidewire lumen;

FIG. 10B is a cross-sectional view of the tubular member of FIG. 10A taken along line 10B—10B;

FIG. 11 is a partial elevational view of a catheter showing the tubular member disposed within the guidewire lumen;

FIG. 12A is a partial elevational view of an alternative embodiment of the tubular member which may be disposed within the catheter's guidewire lumen;

FIG. 12B is a cross-sectional view of the tubular member of FIG. 12A taken along line 12B—12B;

FIG. 12C is a cross-sectional view of the catheter of FIG. 11 taken along line 12C—12C;

FIG. 13 is a cross-sectional view of the catheter of FIG. 11, taken along line 13—13 when the tubular member of FIG. 10A is disposed within the guidewire lumen;

FIG. 14 is a cross-sectional view of the catheter of FIG. 11 taken along line 13—13 when the tubular member of FIG. 12A has been advanced into the guidewire lumen;

FIG. 15 is a is a cross-sectional view of the catheter of FIG. 11 taken along line 13—13 in which a guidewire has been inserted into the lumen of the tubular member;

DETAILED DESCRIPTION OF THE PREFERRED EMBODIMENTS

Figure 4:
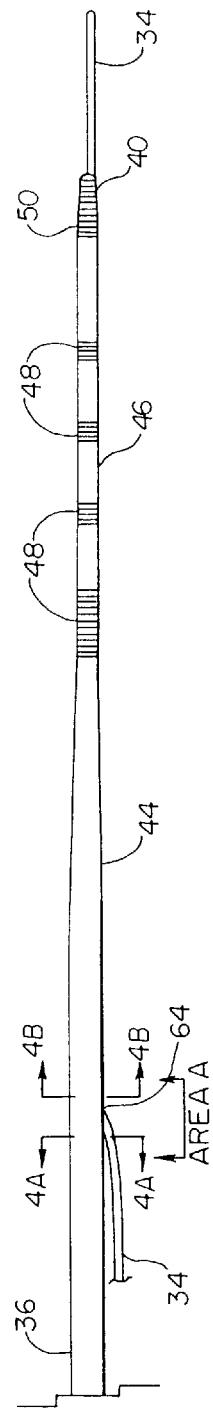
FIG. 4 is a partial elevational view of another embodiment of the catheter in accordance with the present invention.

The following detailed description should be read with reference to the drawings in which similar elements in different drawings are numbered the same. The drawings, which are not necessarily to scale, depict illustrative embodiments and are not intended to limit the scope of the invention.

FIG. 1 shows a partial elevational view of a catheter assembly 30 in accordance with the present invention. The catheter assembly 30 is used in catheter procedures for accessing targeted anatomical regions through the alimentary canal. The present invention incorporates features which allow rapid exchange of catheter by a single operator. The catheter of the present invention allows shorter length guidewires to be used, resulting in procedures which require less medical personnel, are less time consuming, and less costly. Additionally, the present invention is adaptable to most catheter devices used for catheter procedures within the alimentary canal.

Catheter assembly 30 includes a catheter 32 having a guidewire 34 passing through a portion thereof. Catheter 32 includes a shaft 36 having a proximal end 38 and a distal end 40. Operably connected to the proximal end 38 of the shaft 36 is a hub assembly 42. Hub assembly 42 couples to ancillary devices allowing access to a lumen within shaft 36. Shaft 36 is preferably formed in an extrusion process. Shaft 36 may be formed of an extruded polymeric material. In one embodiment, the preferred polymeric material is polytetrafluoroethylene, polyether block amide, nylon or a combination or blend of these. Catheters which are contemplated include, but are not limited to, cannulas, sphinctertomes, cytology devices, and devices for stone retrieval and stent placement.

Shaft 36 is a generally tubular shaped member having a generally uniform outer shape at its proximal end. Shaft 36 may be sized for slidable passage through the lumen of an endoscope. Shaft 36 includes a distal taper 44 which tapers to a tip region 46. Tip region 46 may include high contrast, color-coded distal markers 48, and a radiopaque distal tip 50 for fluoroscopic visualization of tip region 46 during a catheter procedure.

Shaft 36 further includes a proximal port or opening 52 located proximal of distal end 40. Proximal opening 52 allows access to shaft 36 for passage of guidewire 34 through shaft 36. FIG. 1A is a cross-sectional view of shaft 36 taken along line 1A—1A at a location proximal of proximal opening 52. Proximal to proximal opening 52, guidewire 34 is positioned adjacent the catheter shaft 36.

Extending longitudinally between the shaft proximal end 38 and distal end 40 is an ancillary lumen 54 and an ancillary lumen 56. Ancillary lumen 54 and ancillary lumen 56 may be injection lumens, allowing for high contrast media flow capability for bubble-free opacification and for excellent visualization of a desired anatomical region. Additionally or alternatively, ancillary lumen 54 and/or ancillary lumen 56 may be used for other ancillary devices, such as a cutting wire lumen or a retrieval balloon lumen.

Referring to FIG. 1B, a cross-sectional view of shaft 36 taken along line 1B—1B of FIG. 1 is shown. A guidewire lumen 58 extends between proximal opening 52 and distal end 40. Guidewire 34 may enter guidewire lumen 58 at proximal opening 52. Guidewire lumen 58 is sized for slidable receipt and passage of guidewire 34 through guidewire lumen 58. Referring to FIG. 1C, guidewire lumen 58 extends through distal taper 44 and tip region 46.

Although it is recognized that proximal opening 52 may be located at any location distal of proximal end 38, proximal opening 52 is preferably located between 10 and 40 cm from distal end 40. Guidewire lumen 58 is a tubular member which is carried adjacent shaft 36 ancillary lumen 54 and ancillary lumen 56. Guidewire lumen 58 maybe formed integral with shaft 36, or alternatively, guidewire lumen 58 maybe part of a separate tubular member which is coupled to the shaft 36 as shown in FIG. 1D.

Now referring to FIGS. 1E and 1F, an alternative embodiment of the catheter depicted in FIG. 1 is illustrated. The catheter shaft 36 of FIG. 1E incorporates a proximal guidewire opening which, in conjunction with the catheter, forms a circular cross section which allows for easy insertion of the guidewire. As depicted in FIG. 1F, the guidewire lumen 58 can include a larger proximal opening which funnels down to the size of the guidewire lumen 58 which extends distal to the distal end of the catheter shaft 36.

Guidewire lumen 58 allows rapid exchange of catheter 32 when an alternative catheter is necessary during a procedure. Shorter length guidewires may be used since guidewire 34 does not pass through proximal end 38 and hub assembly 42, but rather exits the catheter shaft 36 at proximal opening 52 located substantially distal from proximal end 38. The unique catheter construction in accordance with the present invention will reduce catheter therapeutic and diagnostic procedure time since catheter device exchanges may be performed relatively more easily and quickly by a single operator. Additional personnel and time associated with maintaining the placement of a conventional (approximately 400 cm) a guidewire within the targeted anatomical region is eliminated, reducing the overall costs of the procedure.

Referring to FIG. 2, a partial elevational view of a distal portion of catheter shaft 36 is shown. Shaft 36 may further include a weakened area 60. The weakened area 60 extends longitudinally along guidewire lumen 58 (not shown) between proximal opening 52 and distal end 40.

When guidewire 34 is positioned within guidewire lumen 58, weakened area 60 allows guidewire 34 to be removed from guidewire lumen 58 by "peeling away" guidewire 34 from catheter shaft 36. Weakened area 60 may include less catheter material than the remaining portion of shaft 36, or may be perforated, cut or slit.

Another embodiment of the present invention is shown generally in FIG. 3. FIG. 3 is a partial elevational view of catheter 32, which may be a "convertible" catheter design. In catheter 32, shaft 36 includes an opening 52 which is a skive port 62 for access to guidewire lumen 58. Catheter 32 is a convertible catheter design in that an existing catheter may be modified to include skive port 62. As a convertible catheter design, skive port 62 is formed by cutting an opening in shaft 36 for access to guidewire lumen 58. It is recognized that catheter 32 may be manufactured to include skive port 62.

Referring to FIG. 3A, proximal to skive port 62 catheter shaft 36 includes ancillary lumen 54 and ancillary lumen 56 as previously described herein. Additionally, shaft 36 includes guidewire lumen 58 extending between proximal end 38 and distal end 40, including between skive port 62 and proximal end 38. Referring to FIG. 3B, guidewire 34 may access guidewire lumen 58 at skive port 62 and extend through the guidewire lumen 58 emerging from distal end 40.

With this embodiment, conventional guidewire techniques may be used for positioning and exchanging catheter 32 within a patient's alimentary canal system. Further, the convertible catheter design incorporates features which allow rapid exchange of catheters by a single operator. Skive port 62 opening 52 allows catheter 32 to be used in rapid exchange of catheter 32 when an alternative catheter is necessary during a procedure. By allowing the guidewire 34 to enter the guidewire lumen 58 at a location distal from the proximal end 38, relatively shorter guidewires maybe used during catheter procedures within the alimentary canal system, resulting in a more efficient and less costly procedure.

Figure 4B:
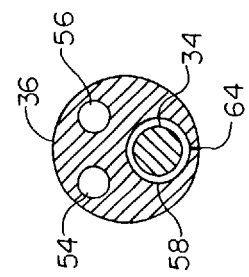
FIG. 4B is a cross-sectional view of the catheter of FIG. 4 taken along line 4B—4B.
Figure 4A:
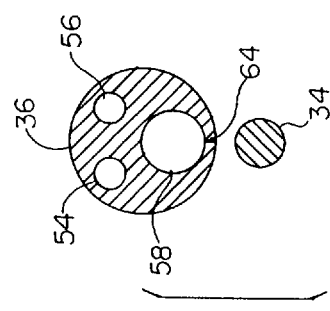
FIG. 4A is a cross-sectional view of the catheter of FIG. 4 taken along line 4A—4A.

It is recognized that other means for accessing the guidewire lumen 58 at a location distal from the proximal end 38 are contemplated within the scope of the present invention. Referring to FIG. 4, a weakened location or slit 64 is shown within area A for accessing the guidewire lumen 58. Referring to FIG. 4A, proximal to the slit 64, the guidewire may be positioned adjacent the catheter shaft 36. Guidewire 34 enters guidewire lumen 58 at slit 64 for passage of guidewire 34 through the guidewire lumen 58. Referring to FIG. 4B, guidewire 34 is slidably contained within the guidewire lumen 58 at a location distal of the slit 64. With this embodiment, since guidewire lumen 58 may extend longitudinally from the proximal end 38 to the distal end 40, conventional guidewire techniques may also be used during the catheter procedure.

Figure 5:
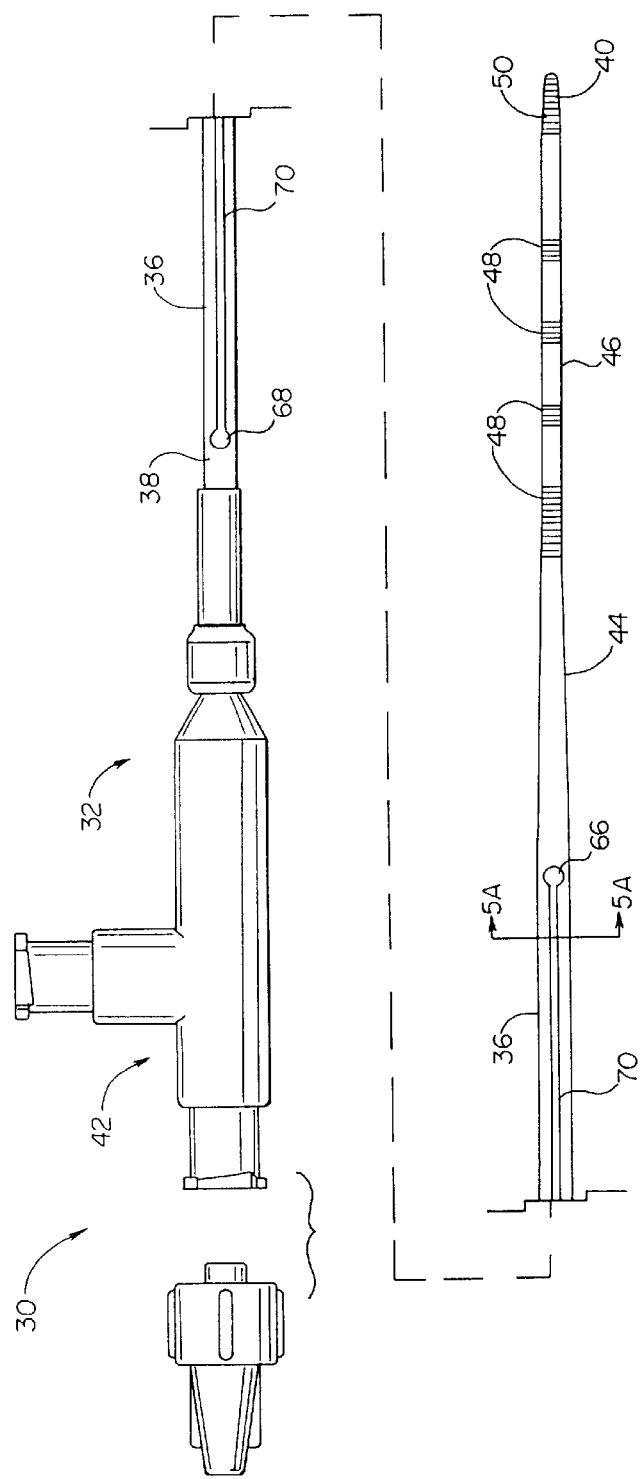
FIG. 5 is a partial elevational view of another embodiment of the catheter in accordance with the present invention.

Referring to FIG. 5, another embodiment of the catheter of the present invention incorporating features which allow rapid exchange of catheters by a single operator is generally shown. The catheter assembly 30 includes a "port and channel" configuration. For access to guidewire lumen 34, shaft 36 includes a first opening or intermediate port 66 located proximal of the distal end 40. A second opening or proximal port 68 is located proximal of the intermediate port 66 and proximal of distal end 40. Extending between the intermediate port 66 and proximal port 68 is a longitudinal channel 70.

Figure 5A:
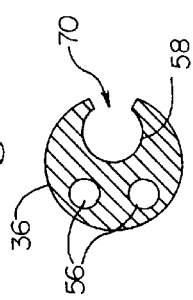
FIG. 5A is a cross-sectional view of the catheter of FIG. 5 taken along line 5A—5A.

Guidewire lumen 34 extends longitudinally between proximal end 38 and distal end 40. Referring to FIG. 5A, channel 70 is located within the wall of catheter shaft 36, providing access to guidewire lumen 58 between proximal port 68 and intermediate port 66. Preferably, channel 70 includes a radial opening extending between proximal port 68 and intermediate port 66. It is also recognized that channel 70 may be a weakened area within the wall of the catheter shaft, a perforated area, or a slit which extends between proximal port 68 and intermediate port 66.

In one embodiment, intermediate port 66 is located near distal end 40, and proximal port 68 is located near proximal end 38. Referring to FIG. 6, the distal end of guidewire 34 may be inserted within the intermediate port 66 (not shown), passing through guidewire lumen 58 and emerging from the catheter 32 distal end 40. Referring also to FIG. 6A, guidewire 34 may then be snapped through channel 70 into guidewire lumen 58 with the proximal end of the guidewire 34 exiting the proximal port 68. With this "port and channel" design, both conventional and rapid exchange techniques may be used.

Figure 7:
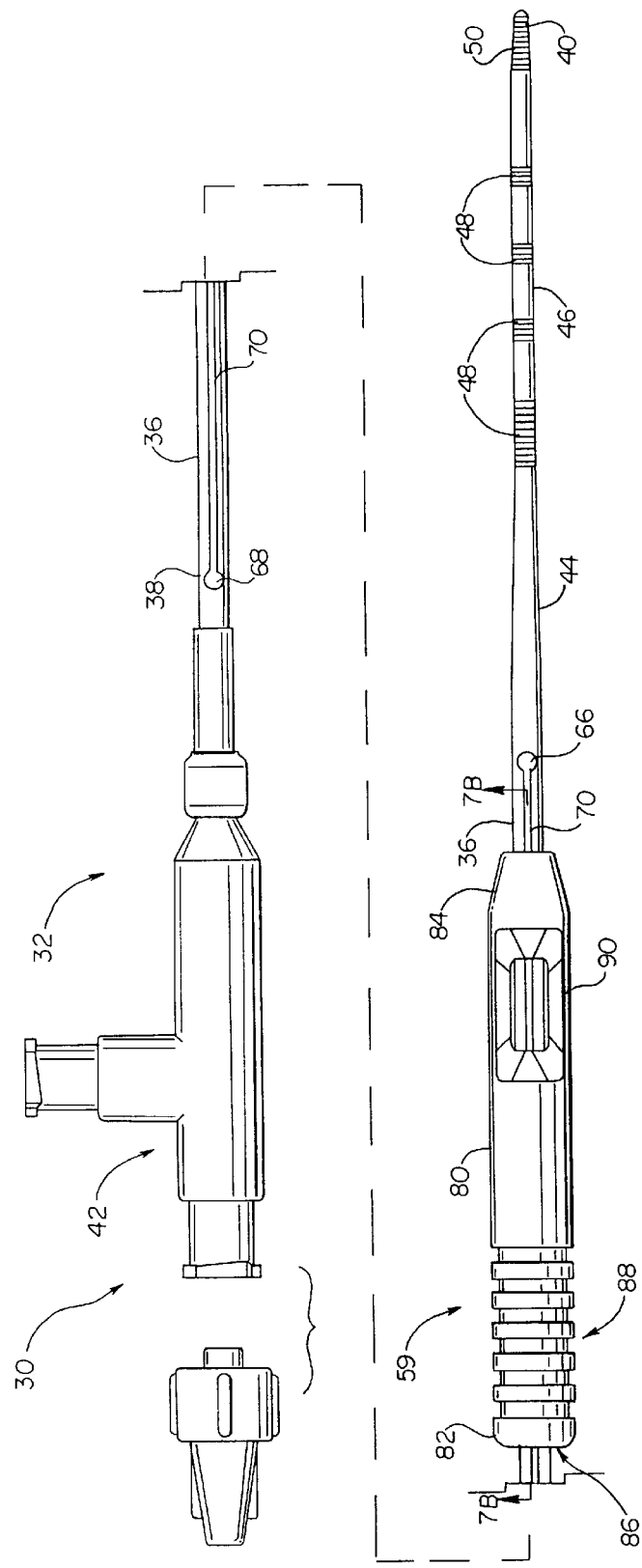
FIG. 7 is a partial elevational view of a catheter assembly showing a guidewire loading tool for use in conjunction with the catheter of FIGS. 5 and 6.

FIG. 7 shows a partial elevational view of the catheter assembly 30 in accordance with the present invention including one preferred embodiment of a tool 59. Tool 59 aids in guiding guidewire 34 during a catheter procedure. Tool 59, shown positioned over catheter shaft 36, includes a body member 80 having a generally tubular shape. The body member 80 includes a proximal end 82, a distal end 84, and a lumen 86 extending longitudinally therethrough. The lumen 86 is sized for slidable receipt of catheter shaft 36. Located near the proximal end 82 of tool 59 is a gripping mechanism 88. Gripping mechanism 88 aids a user in gripping tool 59 during use of tool 59. Located proximal to the distal end 84 of tool 59 is guidewire opening 90. Guidewire opening 90 is brought in communication with a desired port or opening along the catheter 36 shaft to aid in guiding a guidewire (such as guidewire 34) into guidewire lumen 58.

Figure 7A:
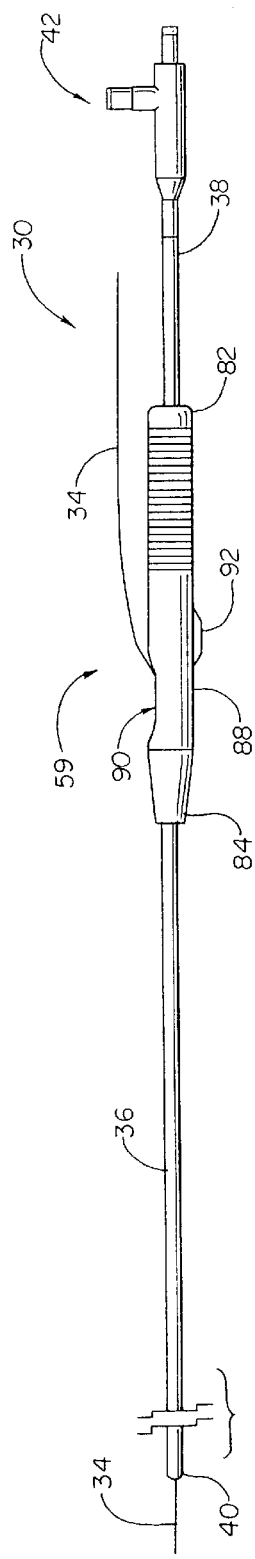
FIG. 7A is an alternative partial elevational view of the catheter assembly of FIG. 7 showing an application of the present invention.
Figure 7B:
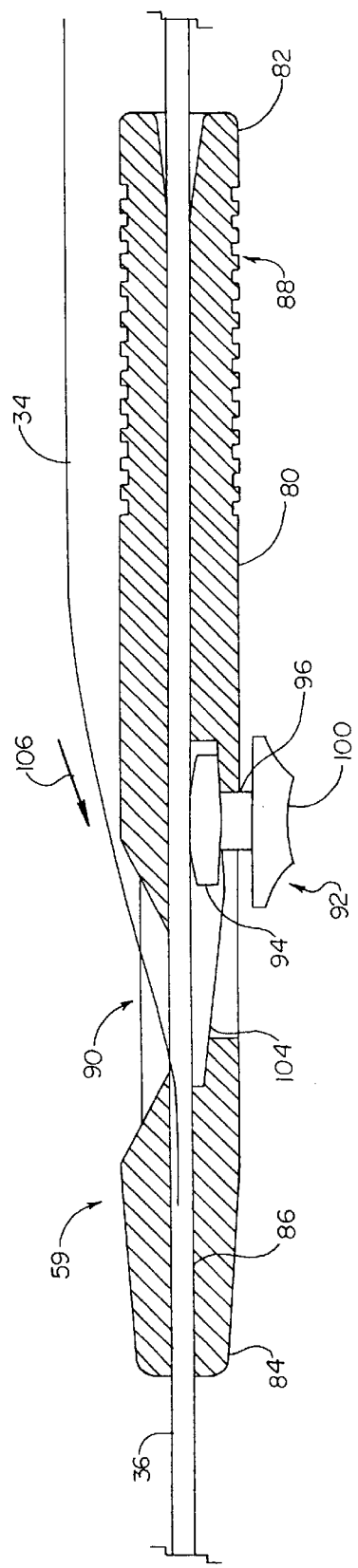
FIG. 7B is a partial cross-sectional view of the catheter of FIG. 7 taken along line 7B—7B, showing a first guidewire tool position.

Referring to FIG. 7A, tool 59 further includes a locking mechanism 92. Referring to FIG. 7B, which is a cross-sectional view of the tool 59 shown in FIG. 7A, locking mechanism 92 further includes a locking head 94, a stem 96 and an operating mechanism 100.

Operating mechanism 100 is located exterior of body member 80. Operating mechanism 100 is coupled to stem 96. Stem 96 extends through an opening 102 in body member 80, and is coupled to locking head 94. Locking mechanism 92 is moveable within an interior chamber 104 of body member 80.

More specifically, by applying pressure externally to operating mechanism 100, locking head 94 is moveable within interior chamber 104 for moving tool 59 between a locked and unlocked position relative to catheter shaft 36. When positioned in a locked position (as shown in FIG. 7B), tool 59 is locked onto catheter shaft 36. When in an unlocked position, tool 59 allows catheter shaft 36 to pass through lumen 86 and move freely relative to tool 59.

Referring again to FIG. 7A and FIG. 7B, tool 59 is shown in a locked position. In this position, locking head 94 friction locks the catheter shaft 36 within lumen 86. As indicated by directional arrow 106, tool 59 allows the catheter shaft 36 to be held stationary, while guidewire 34 is inserted into the guidewire lumen 58 through an opening or port in the catheter shaft 36 (such as proximal port 66 or intermediate port 68 in FIG. 7).

Figure 7C:
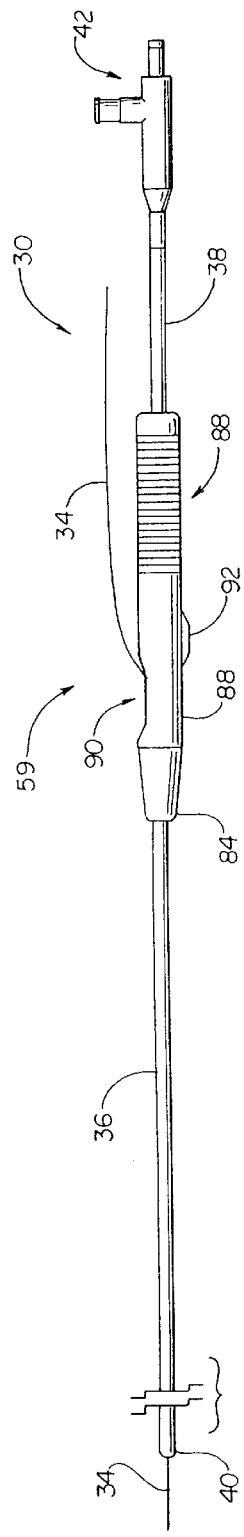
FIG. 7C is a partial elevational view of a catheter assembly showing an application of the present invention.
Figure 7D:
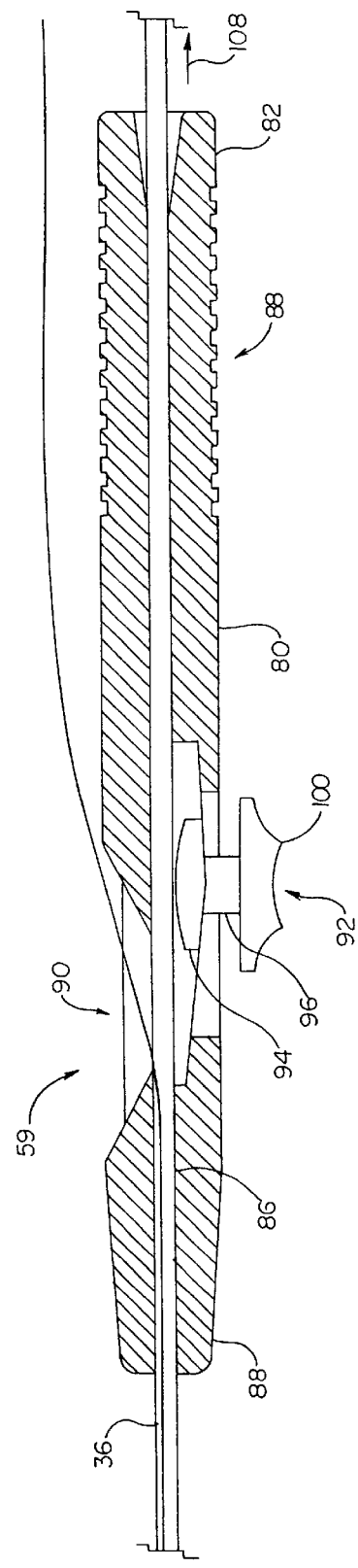
FIG. 7D is a partial cross-sectional view of the catheter of FIG. 7 taken along line 7B—7B showing a second guidewire tool position.

Referring to FIG. 7C, once guidewire 34 is in place during a biliary procedure, it may be necessary to remove the catheter shaft 36. By applying pressure to operating mechanism 100, locking mechanism 92 may be moved to an unlocked position, as shown in FIG. 7D. The guidewire 34 may be held stationary, and the catheter shaft 36 may be removed (indicated by directional arrow 108), allowing the catheter shaft 36 to be removed or "peeled away" from the guidewire 34 while the guidewire 34 remains positioned within the patient's body.

Figure 7E:
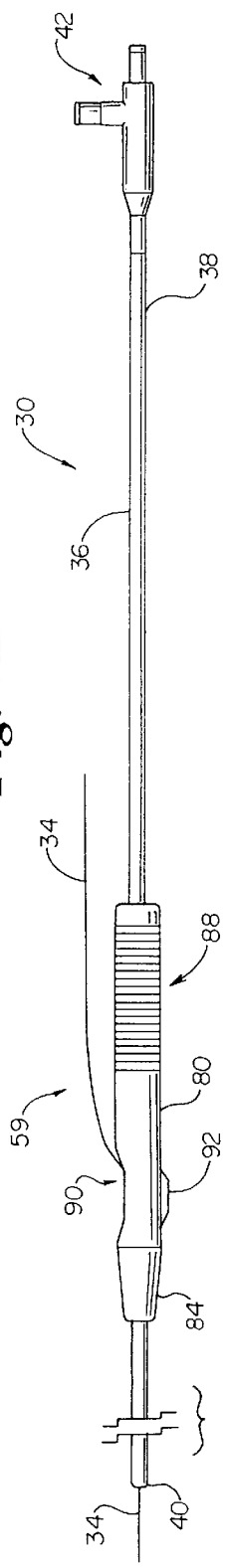
FIG. 7E is a partial elevational view of a catheter assembly showing an application of the present invention.
Figure 7F:
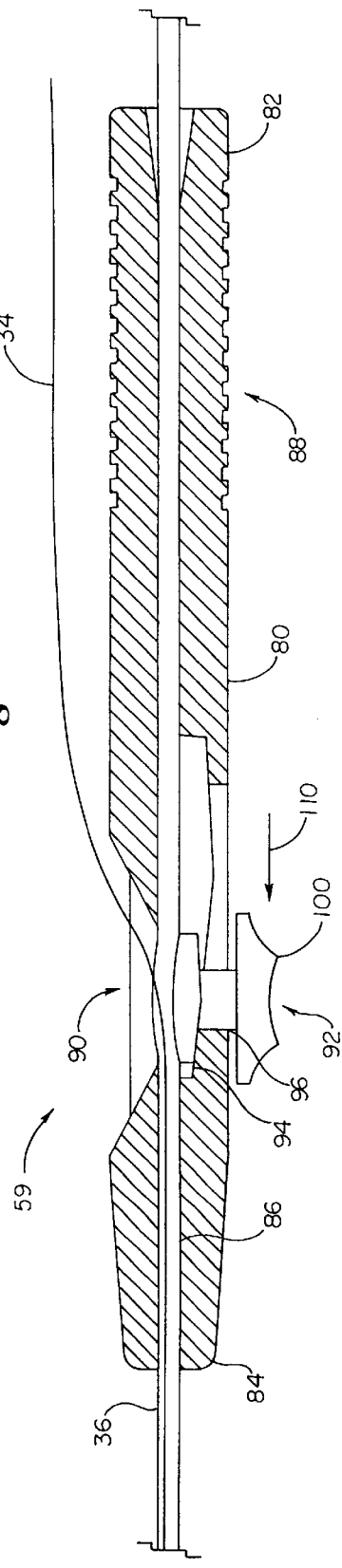
FIG. 7F is a partial cross-sectional view of the catheter of FIG. 7 taken along line 7B—7B, showing a third guidewire tool position.

Referring to FIG. 7E, tool 59 may be used to back load catheter shaft 36 onto guidewire 34 positioned within the patient's biliary tree. Referring to FIG. 7F, to start back loading catheter shaft 36 onto guidewire 34, tool 59 is positioned over the desired opening (such as intermediate opening 68 in the embodiment shown in FIG. 7) and locked to catheter shaft 36 in a deflected position.

By applying pressure to operating mechanism 100 (indicated by directional arrow 110), locking head 94 locks catheter shaft 36 in a "deflected" position. By locking the tool 59 to catheter shaft 36 in a deflected position, tool 59 aids in back loading the catheter shaft 36 onto guidewire 34.

To start back loading, the distal end 40 of catheter shaft 36 is inserted over the proximal end of guidewire 34. As catheter shaft 36 passes over the guidewire 34, the proximal end of guidewire 34 is guided through the catheter intermediate opening 66, through guidewire opening 90, exiting tool 59.

Referring to FIG. 7G, once the proximal end of guidewire 34 is guided through the intermediate opening 66, catheter shaft 36 may continue to be back loaded onto guidewire 34. Referring to FIG. 7H, by returning locking mechanism 92 to an unlocked position, guidewire 34 may be held stationary relative to tool 59, and catheter shaft 36 moves freely within lumen 86 (indicated by directional arrow 112), allowing catheter shaft 36 to be loaded onto guidewire 34. As catheter shaft 36 is loaded onto guidewire 34, the tool 59 aids in guiding guidewire 34 through channel 70 into the guidewire lumen 58 until guidewire 34 exits proximal opening 68.

Tool 59 aids in guiding guidewire 34 through opening 52 (shown in FIG. 1) or "port and channel" proximal port 68, channel 70, and intermediate port 66 (as shown in FIG. 7). Tool 59 allows for gradual introduction of guidewire 34 into the guidewire lumen 58 during an endoscopic procedure. As previously described herein, it is recognized that tool 59 may be used to hold catheter shaft 36 stationary while guidewire 34 is being advanced or retracted during a catheter procedure. Alternatively, it is recognized that tool 59 may be used to hold guidewire 34 in place during a rapid exchange procedure or during advancement or retraction of catheter shaft 36 over guidewire 34.

It is also recognized that a locking device (not shown) maybe located proximate first port 66 or proximate second port 68 to aid in guiding guidewire 34 into guidewire lumen 58 during an endoscopic procedure. The locking device can be similar to the tool 59 as previously described herein. Additionally, it is recognized that tool 59 may be used to hold the catheter shaft 36 in place while guidewire 34 is being advanced or retracted during a catheter procedure. Alternatively, it is recognized that tool 59 maybe used to hold guidewire 34 in place during a rapid exchange procedure, or during advancement or retraction of catheter shaft 36 over guidewire 34.

It is recognized that the rapid exchange technology of the present invention may be utilized in different types of catheter assemblies used within the alimentary canal. Referring to FIG. 8, catheter assembly 30 is used as a rapid exchange retrieval balloon system used for stone retrieval or isolated visualization techniques. Ancillary lumens 54 and 56 (FIG. 1A) are available for passage of retrieval balloon catheter 72 having a balloon 74 located at its distal end, and for passage of dye injection apparatus 76. With this embodiment, the guidewire lumen may be accessed using conventional guidewire techniques through the proximal end of catheter 32 or using rapid exchange techniques.

Referring to FIG. 9, the rapid exchange designs of the present invention may be used for other alimentary canal catheter applications, such as a rapid exchange sphincter catheter used for endoscopic retrograde sphincterotomy, shown using a cutting wire apparatus 78. Again, the guidewire lumen (not shown) may be accessed by conventional guidewire techniques at the proximal end, or alternatively, using the rapid exchange technology of the present invention.

The rapid exchange catheter of the present invention is a multi-lumen catheter. With this invention, the guidewire lumen is isolated from the ancillary lumens allowing for exceptional contrast flow for high quality opacification without the need for guidewire removal. Treatment and therapeutic devices, such as retrieval balloon catheters or catheters having cutting apparatus may be advanced through the ancillary lumens, without interference of a guidewire located within the guidewire lumen. Additionally, isolation of the guidewire lumen from the contrast lumen minimizes the risk of bubble formation during contrast flow and produces a contrast-free guidewire surface for efficient device exchanges.

The rapid exchange biliary catheter of the present invention results in less time consuming and less costly catheter procedures, since a much shorter guidewire may be used and additional personnel are not required to maintain the guidewire position during a catheter procedure. In use in a typical endoscopic procedure, an endoscope is first introduced into the mouth of a patient and is guided through the patient's alimentary canal. Specifically, the endoscope is guided down the esophagus, through the stomach, past the pyloric sphincter of the stomach and into the duodenum. The endoscope has a lumen extending longitudinally between its proximal end and the distal end.

The endoscope is guided through the alimentary canal until the distal end of the endoscope is proximate the target area within the anatomy to receive treatment. In an endoscopic biliary procedure, the endoscope is guided into the duodenum until the opening at the distal end of the endoscope is proximate the papilla of vater. The papilla of vater is located between the sphincter of oddi, which leads to the common bile duct, hepatic, and pancreatic ducts. The proximate end of the endoscope extends and remains outside the mouth of the patient.

With general reference to the various embodiments shown in FIGS. 1–7, once the endoscope is in proper position, guidewire 34 is inserted into the proximal opening of the endoscope and advanced through the lumen of the endoscope until guidewire 34 distal end emerges from the opening at the distal end of the endoscope. The distal tip of guidewire 34 may be guided through the orifice leading to the papilla of vater for access into the biliary tree.

Once the distal end of guidewire 34 is positioned within the biliary tree (including the common bile, hepatic or pancreatic ducts), rapid exchange catheter 32, in accordance with the present invention, may be back-loaded onto guidewire 34. Distal end 40 of catheter 32 is loaded onto the proximal end of guidewire 34. Rapid exchange catheter 32 is advanced over guidewire 34, until the distal end 40 exits the distal end of the endoscope. Within the endoscope, distal from opening 52, the guidewire passes through guidewire lumen 58, and proximal to opening 52, the guidewire is positioned adjacent catheter shaft 36.

Distal end 40 of catheter 32 tracks guidewire 34 through the orifice leading to the papilla of vater, and into the desired duct, such as the common bile duct. Once distal end 40 of catheter 32 is in position in the common bile duct, catheter procedures may be performed, such as injecting a contrast media, such as radiopaque dye, through ancillary lumen 54 and ancillary lumen 56 into the common bile duct for visualization of the duct.

Since the proximal end of guidewire 34 exits the guidewire lumen 58 at a location distal of the catheter 32 proximal end 38, shorter guidewires maybe used by the physician as previously described herein. In one embodiment, a 250 cm guidewire is used. The use of the shorter guidewire eliminates many disadvantages of using longer guidewires which were approximately 400 cm in length, while maintaining or improving the efficiency and outcome of the procedure.

Alternatively, if a guidewire 34 has not been previously positioned within the biliary tree, rapid exchange catheter 32 may be used to establish access to the targeted anatomy location within the alimentary canal. Catheter 32 is passed through the lumen of the endoscope, until distal end 40 is guided up through the orifice into the papilla of vater, and into the desired duct, such as the common bile duct. The guidewire 34 is then inserted into the endoscope lumen adjacent catheter 32. Guidewire 34 is advanced through opening 52 into guidewire lumen 58 to the targeted area, such as the common bile duct.

Once guidewire 34 is in position, and the desired catheter procedure has been completed, rapid exchange catheter 32 can be exchanged or removed from the endoscope, while leaving guidewire 34 in position for other catheter procedures. Catheter 32 is removed from guidewire 34 by tracking catheter 32 back over guidewire 34 until guidewire lumen 58 is retracted completely off the proximal end of guidewire 34.

Referring to the embodiment of FIG. 2, if catheter 32 includes weakened area 60, once opening 52 is outside of the proximal end of the endoscope, catheter 52 may be "peeled away" from guidewire 34 until catheter 32 is completely removed from guidewire 34.

Although catheter 32 is removed from guidewire 34, the position of guidewire 34 is maintained within the targeted anatomy. Other rapid exchange procedures may be performed, such as the catheter assembly 30 of FIG. 8 or FIG. 9 without having to re-establish a path to the target area of the anatomy to receive therapeutic or diagnostic treatment. These catheter assemblies may be loaded onto guidewire 34 using the same rapid exchange procedures as previously described herein.

If a convertible catheter (as shown in FIG. 3) or "slit" catheter (as shown in FIG. 4) are used, the physician may alternate between conventional and rapid exchange guidewire procedures since guidewire lumen 58 within these devices extend from distal end 40 to proximal end 38.

If catheter 32 further includes a "port and channel" type configuration (FIG. 5), as rapid exchange catheter 32 is back-loaded onto guidewire 34, the proximal end of guidewire 34 exits the distal or first port 66 of the catheter 32. As catheter 32 is advanced over guidewire 34, the guidewire is "snapped" into guidewire lumen 58 via channel 70. When catheter 32 is fully advanced over guidewire 34, guidewire 34 exits guidewire lumen 58 through proximal or second port 68.

With the "port and channel" technology, when catheter 32 is positioned within the endoscope, guidewire 34 is not located adjacent catheter shaft 36, but rather is positioned within guidewire lumen 58. Guidewire 34 exits guidewire lumen 58 at second port 68, which is located outside of and proximal to the proximal end of the endoscope. With this configuration, additional working space is not required for guidewire 34 to lie adjacent catheter 32 within the endoscope lumen. This configuration allows for more room within the working space of the endoscope, allowing for larger ancillary lumens within catheter 32 itself.

The "port and channel" catheter configuration may be manufactured as a catheter unit, or, alternatively, existing catheter devices may be converted or modified to include the "port and channel" design. Upon retraction of catheter 32 from the endoscope, guidewire 34 is peeled away from the endoscope via channel 70 until first port 66 is retracted from the proximal end of the endoscope. The short length of catheter 32 distal of first port 66, which does not include access channel 70, is retracted completely off the proximal end of guidewire 34.

As previously described herein, if guidewire 34 is not in position within the targeted anatomical location, the rapid exchange catheter 32 may be used to cannulate the path to the targeted location within the patient's anatomy, such as cannulating the papilla of vater for access to the ducts of the biliary tree. As previously described herein, the catheter may then be removed, and other rapid exchange devices using the technology of the present invention may be exchanged over the guidewire since the guidewire remains in position within the biliary tree.

As previously described herein, guidewire lumen 58 may be a tubular member which is extruded integral the catheter 32 shaft, or alternatively, guidewire lumen 58 may be a separate tubular member which is coupled to catheter shaft 36. Although in one preferred embodiment guidewire lumen 58 is a tubular member which is located proximate distal end 40 of the catheter shaft 36, it is recognized that guidewire lumen 58 maybe formed anywhere along shaft 36, may be an extension of shaft 36 coupled to the distal end 40, or guidewire lumen 58 may run the entire length of shaft 36.

Another embodiment of the present invention is shown in FIGS. 10–15. FIG. 10A is a partial elevational view of one embodiment of a tubular member 113. Tubular member 113A includes a shaft 115 having a distal opening 119 and a proximal opening 117. In one embodiment, proximal opening 117 is flared to allow easier insertion of a guidewire 34. FIG. 10B is a cross-sectional view of tubular member 113A taken along line 10B—10B of FIG. 10A. As seen in FIG. 10B, a lumen 121 extends between proximal opening 117 and distal opening 119.

FIG. 11 is a partial elevational view of the catheter 32 with the tubular member 113A shown inserted through channel opening 68 of catheter shaft 36 and into guidewire lumen 58, and advanced longitudinally therein. Tubular member 113A includes a distal tip 114 which may extend beyond the distal end of catheter 32, as shown in FIG. 11. Except as described herein, this embodiment is substantially similar in design and use to that described with reference to FIGS. 1–9.

Tubular member 113 serves to convert a catheter having a C-shaped channel design to one having an O-shaped channel design. As best seen in FIG. 13, the tubular member 113A is shown disposed within guidewire lumen 58, thereby converting the catheter from a C-channel design to an O-channel design. A guidewire 34 may enter through proximal opening 117 and be advanced longitudinally therein through distal opening 119 and into position within a body lumen. Tubular member 113, by providing an isolated environment for guidewire 34, secures the guidewire in place within the lumen 121. Thus, tubular member 113 allows for the use of a smaller diameter guidewire than would be possible with a catheter having an unaltered C-channel design, wherein a small diameter guidewire would be at risk of slipping out of the channel 70 to a position exterior to the catheter 32.

Tubular member 113 may therefore be used in a method for exchanging guidewires during a biliary endoscopic procedure. The method includes the step of inserting the tubular member 113 through the channel opening 68 and into the guidewire lumen 58, and advancing it longitudinally therein, preferably before advancing the catheter 32 over the guidewire 34. The catheter 32 is then advanced over the guidewire 34 such that the guidewire 34 is disposed through the lumen 121 of the tubular member 113. The method further includes retracting the guidewire 34 from the tubular member 113 and removing the tubular member 113 from the catheter 32 through the channel 70. A second guidewire, whose diameter may be greater or less than that of the first guidewire, is then advanced through the guidewire lumen 58, wherein a proximal end of the guidewire exits the channel opening 68. In other respects, this method is substantially similar to the methods detailed in the descriptions of FIGS. 1–9.

The distal tip 114 of the tubular member 113 may extend beyond the distal end of the catheter shaft 32 to define a tip which is more flexible and smaller in profile than the distal end of the catheter shaft 32. The distal tip may be used to facilitate intraluminal navigation, cannulation and dilation. As such, not only does the tubular member 113 serve as a C to O channel converter as described previously, but the tubular member 113 may be used as a dilator or a cannula. As a dilator or cannula, the tubular member 113 may have a length sufficient to extend 5 cm beyond the distal end of the shaft and have a tip profile of approximately 3F.

FIG. 12A shows an alternative, preferred embodiment of the tubular member 113. FIG. 12B is a cross-sectional view of tubular member 113B taken along line 12B—12B in FIG. 12A. FIG. 12C is a cross-sectional view of the catheter 32 taken along line 12C—12C of FIG. 11, and reveals the cross-sectional profile of the guidewire lumen 58. Tubular member 113B comprises a tubular shaft 123 formed integral with an outer portion 125. In one embodiment, the outer portion 125 extends along the entire length of tubular member 113B, as shown in FIG. 13A. In another embodiment, outer portion 125 extends only over a portion (e.g., distal portion) of tubular member 113B. The distal tip 114B may have the outer portion 125 removed such that the tubular member 113B may be used as a dilator or a cannula.

FIG. 14 is a cross-sectional view taken along line 13—13 of catheter 32 of FIG. 11 in which tubular member 113B has been advanced into guidewire lumen 58. The cross-sectional profile of tubular member 113B is designed to mate with the cross-sectional profile of the guidewire lumen 58 and channel 70. Designing the cross-sectional profile of tubular member 113 such that it mates with the guidewire lumen 58 and channel 70 is advantageous in that a tighter seal is formed between the two components, thus enhancing the pushability and column strength of the catheter, as well as reducing the amount of fluid leakage through the channel. FIG. 15 is a cross-sectional view taken along line 13—13 of catheter 32 of FIG. 11 in which guidewire 34 has been inserted into the lumen 121 of tubular member 113B. The design and use of tubular member 113B is otherwise substantially the same as tubular member 113A.

FIG. 10A and FIG. 12A disclose specific embodiments of tubular member 113, but it is recognized that other embodiments of a tubular member shaped to convert the catheter's C-channel design to an O-channel design are also within the scope of the present invention.

As tubular member 113 is designed to be disposed within guidewire lumen 58, its outer diameter should accordingly be small enough to fit within the lumen, yet preferably large enough to sit against the wall of the guidewire lumen 58 to avoid slippage out of the channel 70 to the exterior of the catheter 32. Accordingly, a preferred outer diameter of the tubular member is between about 0.025 inches and about 0.040 inches, with a diameter of about 0.035 inches being especially preferred. A preferred inner diameter of tubular member 113 is between about 0.014 inches and about 0.025 inches, with a diameter of about 0.027 inches being especially preferred.

The length of tubular member 113 should preferably be greater than the length of the biliary catheter 32, for example, about 212 cm. In a preferred embodiment, tubular member 113 extends distally about 5 mm past the distal tip of the biliary catheter 32. Those of ordinary skill in the art of biliary catheters will recognize that tubular member 113 may be constructed out of a variety of commonly known materials using conventional techniques.

Figure 16:
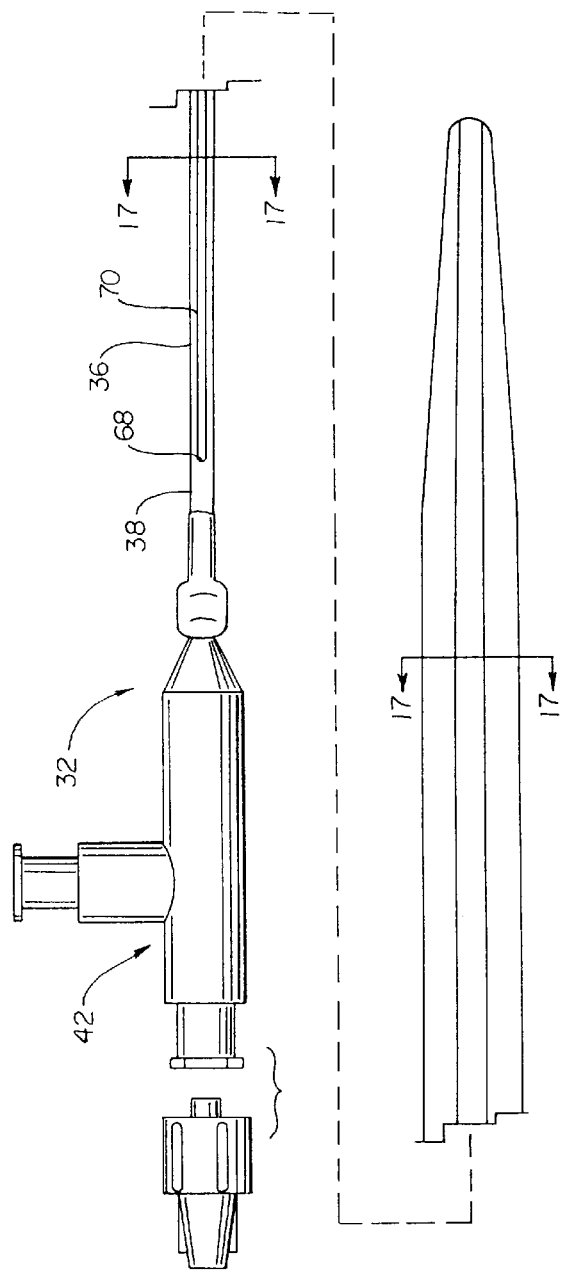
FIG. 16 is a partial elevational view of another embodiment of the catheter in accordance with the present invention.
Figure 17B:
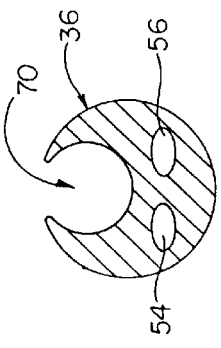
FIG. 17B is a cross-sectional view of the catheter of FIG. 16 taken along line 17—17, showing a channel having a C-shaped cross sectional profile.
Figure 17A:
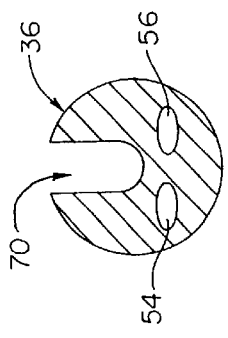
FIG. 17A is a cross-sectional view of the catheter of FIG. 16 taken along line 17—17, showing a channel having a U-shaped cross-sectional profile.

FIG. 16 represents another embodiment of the catheter of the present invention in which the channel 70 extends from the opening 68 through the distal tip of the catheter. In other embodiments, the channel 70 may reach the distal tip of the catheter but not extend through it. This configuration may allow the operator to completely withdraw the catheter without the need for an assistant. FIG. 17A is a cross-sectional view taken along line 17—17 of the catheter shaft 32 in FIG. 16, showing the channel 70 having a U-shaped cross-sectional profile. FIG. 17B is a cross-sectional view taken along line 17—17 of the catheter shaft 32 in FIG. 16, and showing an alternative embodiment in which the channel 70 includes a C-shaped cross-sectional profile. In one embodiment, a proximal portion of the channel 70 includes a U-shaped cross-sectional profile as shown in FIG. 17A, and a distal portion of the channel 70 includes a C-shaped cross-sectional profile as shown in FIG. 17B. In an alternative embodiment, a proximal portion of the channel 70 includes a C-shaped cross-sectional profile as shown in FIG. 17B, while a distal portion of the channel 70 includes a U-shaped cross-sectional profile, as shown in FIG. 17A.

It will be understood, that this disclosure is, in many respects, only illustrative. Changes may be made in details, particularly in matters of shape, size, material, and arrangement of parts without exceeding the scope of the invention. Accordingly, the scope of the invention is as defined within the language of the appended claims.

What is claimed is:

1. A biliary catheter for use in biliary procedures, comprising:
   a first elongate member having an outer surface, a proximal end and a distal end;
   a guidewire lumen disposed within the first elongate member extending from a location proximal the distal end of the first elongate member to a location proximate the distal end of the first elongate member;
   a channel allowing access to the guidewire lumen from the exterior of the catheter and extending longitudinally along the outer surface of the first elongate member, the channel defining a first edge surface and a second edge surface; and
   a second elongate member, having a proximal end and a distal end, including a tubular shaft and defining a lumen therethrough, the second elongate member being disposed within the guidewire lumen and extending longitudinally therein, and having an opening at its proximal end and at its distal end;
   wherein the second elongate member is configured to accept a guidewire and prevent said guidewire from falling out of the guidewire lumen through the channel that allows access to the guidewire lumen from the exterior of the catheter.

2. The biliary catheter of claim 1, wherein the guidewire lumen has a cross-sectional profile and the second elongate member has a cross-sectional profile which mates with the cross-sectional profile of the guidewire lumen.

3. The biliary catheter of claim 2, wherein the second elongate member additionally includes an outer portion comprised of an upper surface and a first side surface and a second side surface, such that the first and second side surfaces of the outer portion engage the first and second edge surfaces respectively.

4. The biliary catheter of claim 1, wherein the second elongate member is removable from the guidewire lumen through the channel.

5. The biliary catheter of claim 1, wherein the second elongate member extends distally from the distal end of the first elongate member.

6. The biliary catheter of claim 1, wherein the second elongate member additionally includes a flared proximal end such that the diameter of the lumen therein is larger at the proximal end of the second elongate member than at a point distal the proximal end.

7. The biliary catheter of claim 1, wherein an inner diameter of the second elongate member is between 0.014 inches and 0.025 inches, and a diameter of the guidewire lumen is between 0.012 inches and 0.028 inches.

8. The biliary catheter of claim 1, wherein an outer diameter of the second elongate member is between 0.025 inches and 0.040 inches.

9. A biliary system comprising:
   a biliary catheter comprising a first elongate member having an outer surface, a proximal end and a distal end, a guidewire lumen carried by the first elongate member extending from a location proximal the distal end of the first elongate member to a location proximate the distal end of the first elongate member, a channel allowing access to the guidewire lumen from the exterior of the catheter and extending longitudinally along the outer surface, the channel defining a first edge surface and a second edge surface, a first opening being located adjacent to the proximal end of the channel;
   a second elongate member, having a proximal end and a distal end, including a tubular shaft and defining a lumen therethrough, the second elongate member being disposed within the guidewire lumen and extending longitudinally therein, and having an opening at its proximal end and at its distal end; and
   a guidewire being disposed through the first opening and into the guidewire lumen, wherein the guidewire is disposed within the second elongate member;

wherein the second elongate member is configured to prevent said guidewire from falling out of the guidewire lumen through the channel that allows access to the guidewire lumen from the exterior of the catheter.

10. A method of using a biliary catheter comprising the steps of:

providing a catheter comprising a first elongate member having a proximal end and a distal end, a guidewire lumen carried by the first elongate member extending from a location proximal the distal end of the elongate member to a location proximate the distal end of the member, the first elongate member including a channel extending longitudinally along the first elongate member, and allowing access from the exterior of the catheter into the guidewire lumen, and defining a first edge surface and a second edge surface longitudinally along the length of the channel;

providing a second elongate member comprising a tubular shaft having a proximal end and a distal end, including an opening at both the proximal end and the distal end and defining a lumen therethrough;

inserting the second elongate member through the channel and into the guidewire lumen of the first elongate member; and advancing the second elongate member longitudinally therein.

11. The method of claim 10, wherein the first elongate member includes a cross-sectional profile, and the second elongate member includes an orientation with respect to the first elongate member, the second elongate member comprising a tubular member, such that the second elongate member possesses a cross-sectional profile which mates with the cross-sectional profile of the first elongate member, the method further comprising the step of:

mating the first elongate member with the second elongate member.

12. The method of claim 11, wherein the second elongate member comprises a tubular member integral with a substantially semi-circularly shaped outer portion, the outer portion comprised of an upper surface and a first and a second side surface, the method further comprising the step of:

adjusting the orientation of the second elongate member until the first and second side surfaces of the outer portion engage the first and second edge surfaces respectively of the first elongate member.

13. The method of claim 10, additionally comprising the steps of:

inserting a guidewire into the lumen of the second elongate member and extending it longitudinally therethrough; and advancing the catheter over the guidewire, wherein a proximal end of the guidewire extends from a proximal region of the first elongate member, and a distal end of the guidewire extends distally from the first elongate member.

14. The method of claim 13, additionally comprising the steps of:

retracting the guidewire from the second elongate member;

removing the second elongate member from the guidewire lumen of the first elongate member; and inserting a second guidewire into the guidewire lumen of the first elongate member and advancing it therethrough, wherein a proximal end of the second guidewire extends from a proximal region of the first elongate member, and a distal end of the guidewire extends distally from the first elongate member.

15. The method of claim 14, additionally comprising the step of selecting the guidewires such that a diameter of the second guidewire is greater than a diameter of the first guidewire.

16. The method of claim 14, additionally comprising the step of selecting the guidewires such that a diameter of the second guidewire is less than a diameter of the first guidewire.

17. The method of claim 10, wherein the distal end of the second elongate member is advanced beyond the distal end of the first elongate member.

* * * * *